US 11,117,119 B2

(12) United States Patent
Suh et al.

(10) Patent No.: US 11,117,119 B2
(45) Date of Patent: Sep. 14, 2021

(54) CATALYST FOR OXIDATIVE DEHYDROGENATION AND METHOD OF PREPARING THE SAME

(71) Applicant: LG CHEM, LTD., Seoul (KR)

(72) Inventors: Myung Ji Suh, Daejeon (KR); Yoon Jae Min, Daejeon (KR); Dong Hyun Ko, Daejeon (KR); Kyong Yong Cha, Daejeon (KR); Se Won Baek, Daejeon (KR); Jun Kyu Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 976 days.

(21) Appl. No.: 15/540,425

(22) PCT Filed: Nov. 30, 2016

(86) PCT No.: PCT/KR2016/013919
§ 371 (c)(1),
(2) Date: Jun. 28, 2017

(87) PCT Pub. No.: WO2017/099411
PCT Pub. Date: Jun. 15, 2017

(65) Prior Publication Data
US 2018/0333702 A1    Nov. 22, 2018

(30) Foreign Application Priority Data

Dec. 9, 2015  (KR) .................. 10-2015-0174676
Dec. 15, 2015  (KR) .................. 10-2015-0179406

(51) Int. Cl.
*B01J 21/00*    (2006.01)
*B01J 29/00*    (2006.01)
(Continued)

(52) U.S. Cl.
CPC .......... *B01J 23/8892* (2013.01); *B01J 21/12* (2013.01); *B01J 21/16* (2013.01); *B01J 23/005* (2013.01);
(Continued)

(58) Field of Classification Search
CPC ...... B01J 23/8892; B01J 21/12; B01J 23/005; B01J 37/033; B01J 37/038; B01J 35/006;
(Continued)

(56) References Cited

U.S. PATENT DOCUMENTS 4,440,874 A    4/1984   Thompson
5,041,401 A    8/1991   Schoennagel et al.
(Continued)

FOREIGN PATENT DOCUMENTS

CN    1686793 A     10/2005
CN    103025425 A    4/2013
(Continued)

OTHER PUBLICATIONS

Sifontes, Ángela B. et al. "Preparation of ?-alumina foams of high surface area employing the polyurethane sponge replica method." Latin American Applied Research 40 (2010): 185-191. (Year: 2010).*

(Continued)

*Primary Examiner* — Haytham Soliman
(74) *Attorney, Agent, or Firm* — Dentons US LLP

(57) ABSTRACT

The present invention relates to a catalyst for oxidative dehydrogenation and a method of preparing the same. More particularly, the present invention provides a catalyst for oxidative dehydrogenation having a porous structure which may easily control heat generation due to high-temperature and high-pressure reaction conditions and side reaction due to the porous structure and thus exhibits superior product selectivity, and a method of preparing the catalyst.

10 Claims, 1 Drawing Sheet

POROUS RUBBER

POROUS ALUMINUM SILICATE SUPPORT

CATALYST FOR OXIDATIVE DEHYDROGENATION

(51) Int. Cl.

| | | |
|---|---|---|
| *B01J 23/889* | (2006.01) | |
| *B01J 23/78* | (2006.01) | |
| *B01J 23/80* | (2006.01) | |
| *B01J 37/00* | (2006.01) | |
| *B01J 21/12* | (2006.01) | |
| *B01J 23/00* | (2006.01) | |
| *B01J 37/03* | (2006.01) | |
| *B01J 35/00* | (2006.01) | |
| *B01J 35/04* | (2006.01) | |
| *B01J 21/16* | (2006.01) | |
| *B01J 35/10* | (2006.01) | |
| *B01J 37/08* | (2006.01) | |
| *C07C 5/48* | (2006.01) | |

(52) U.S. Cl.
CPC ............... *B01J 23/78* (2013.01); *B01J 23/80* (2013.01); *B01J 35/0006* (2013.01); *B01J 35/006* (2013.01); *B01J 35/04* (2013.01); *B01J 35/108* (2013.01); *B01J 37/0018* (2013.01); *B01J 37/0036* (2013.01); *B01J 37/033* (2013.01); *B01J 37/035* (2013.01); *B01J 37/038* (2013.01); *B01J 37/08* (2013.01); *C07C 5/48* (2013.01); *B01J 2523/00* (2013.01); *C07C 2521/12* (2013.01); *C07C 2523/78* (2013.01); *C07C 2523/80* (2013.01); *C07C 2523/889* (2013.01)

(58) Field of Classification Search
CPC ........ B01J 37/0036; B01J 35/04; B01J 21/16; B01J 35/0006; B01J 35/108; B01J 37/035; B01J 37/08; B01J 23/80; B01J 37/0018; B01J 23/78; B01J 2523/00; C07C 5/48; C07C 2521/12; C07C 2523/78; C07C 2523/80; C07C 2523/889
USPC .......................................................... 502/74
See application file for complete search history.

(56) References Cited

U.S. PATENT DOCUMENTS

| | | | |
|---|---|---|---|
| 8,226,740 B2 | 7/2012 | Chaumonnot et al. | |
| 2002/0183407 A1 | 12/2002 | Yoon et al. | |
| 2003/0228457 A1 | 12/2003 | Hasegawa et al. | |
| 2013/0158325 A1* | 6/2013 | Kwon | C07C 5/3332 |
| | | | 585/625 |
| 2014/0271384 A1 | 9/2014 | Nazarpoor et al. | |
| 2014/0271390 A1 | 9/2014 | Nazarpoor | |

FOREIGN PATENT DOCUMENTS

| | | | |
|---|---|---|---|
| CN | 104001533 A | 8/2014 | |
| CN | 102974357 B | 9/2015 | |
| KR | 10-2002-0027790 A | 4/2002 | |
| KR | 10-2007-0039393 A | 4/2007 | |
| KR | 10-0847206 B1 | 7/2008 | |
| KR | 10-2009-0124384 A | 12/2009 | |
| KR | 10-0950373 B1 | 3/2010 | |
| KR | 10-2012-0009687 A | 2/2012 | |
| KR | 10-2015-0058055 A | 5/2015 | |
| WO | 03/026787 A2 | 4/2003 | |
| WO | WO-2013057319 A2 * | 4/2013 | ............ C10G 2/332 |
| WO | 2015/025286 A2 | 2/2015 | |

OTHER PUBLICATIONS

Toledo, J. A. et al. "Oxidative dehydrogenation of 1-butene over Zn—Al ferrites", Journal of Molecular Catalysis A: Chemical, 1997, vol. 125, No. 1, pp. 53-62.
Gibson, Michael A. "Oxidative Dehydrogenation of Butenes over Magnesium Ferrite Catalyst Deactivation Studies", Journal of Catalysis 1976, vol. 41, No. 3, pp. 431-439.
Chu, Catalyst Engineering, ISBN 7-5614-3384-0 (2006), 2 Pages.
Xiaoyong, et al.: "The research on carrier of mesh porous ceramics made by steep handicraft", Journal of Pingxiang College, No. 6, pp. 72-77 (Dec. 31, 2006).
Lee et al., "Effect of Divalent Metal Component (MeII) on the Catalytic Performance of Me(II)Fe2O4 Catalysts in the Oxidative Dehydrogenation of n-Butene to 1,3-Butadiene", Catal. Lett., vol. 124, pp. 364-368 (2008).

* cited by examiner

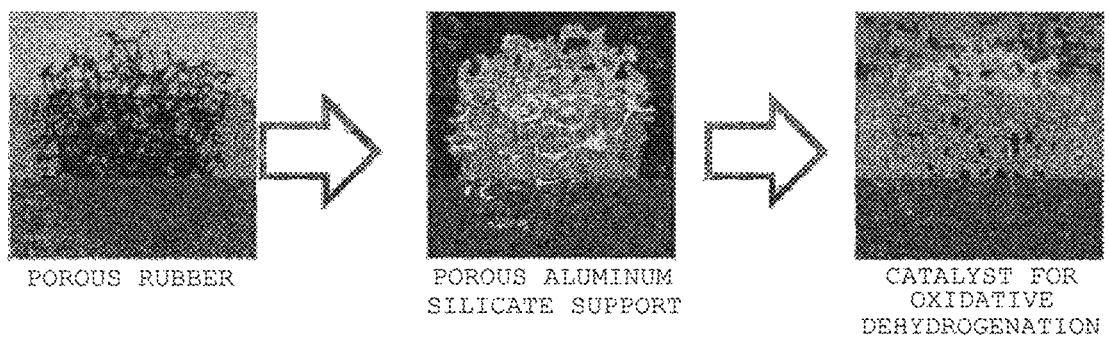

CATALYST FOR OXIDATIVE DEHYDROGENATION AND METHOD OF PREPARING THE SAME

TECHNICAL FIELD

Cross-Reference to Related Applications

This application is a National Stage Entry of International Application No. PCT/KR2016/013919 filed on Nov. 30, 2016, and claims the benefit of Korean Patent Application No. 10-2015-0174676, filed on Dec. 9, 2015, and Korean Patent Application No. 10-2015-0179406, filed on Dec. 15, 2015, all of which are hereby incorporated by reference in their entirety for all purposes as if fully set forth herein.

The present invention relates to a catalyst for oxidative dehydrogenation and a method of preparing the same. More particularly, the present invention relates to a catalyst for oxidative dehydrogenation having a porous structure which may easily control heat generation due to high-temperature and high-pressure reaction conditions and side reaction due to the porous structure and thus exhibits superior product selectivity, and a method of preparing the catalyst.

BACKGROUND ART

Demand for 1,3-butadiene, which is an intermediate in petrochemical products, and the value thereof are gradually increasing throughout the world. To produce such 1,3-butadiene, methods, such as naphtha cracking, direct butene dehydrogenation, and oxidative dehydrogenation of butene, have been used. However, in the case of naphtha cracking, energy consumption is high due to high reaction temperature. In addition, since naphtha cracking is not a process specifically designed for production of 1,3-butadiene production, other basic oils, other than 1,3-butadiene, are disadvantageously produced as surplus products. Meanwhile, direct dehydrogenation of normal-butene is thermodynamically unfavorable. In addition, since direct dehydrogenation of normal-butene is an endothermic reaction, high-temperature and low-pressure conditions are required to produce 1,3-butadiene in a high yield. Accordingly, direct dehydrogenation of normal-butene is not suitable as a commercial process for producing 1,3-butadiene.

Meanwhile, since, in the case of oxidative dehydrogenation of butene wherein butene reacts with oxygen in the presence of a metal oxide catalyst to generate 1,3-butadiene and water, stable water is generated, oxidative dehydrogenation of butene is thermodynamically advantageous. In addition, since oxidative dehydrogenation of butene is an exothermic reaction unlike direct dehydrogenation of butene, oxidative dehydrogenation of butene may produce 1,3-butadiene in a high yield even at low reaction temperature, compared to direct dehydrogenation of butene. In addition, since oxidative dehydrogenation of butene does not require additional heat supply, oxidative dehydrogenation of butene may be considered an effective production process that produces only 1,3-butadiene and thus satisfies demand for 1,3-butadiene. However, in the case of oxidative dehydrogenation, a high calorific value due to a high-temperature reaction condition affects the activity and durability of a metal oxide catalyst, whereby selectivity for 1,3-butadiene is decreased. In addition, since a calorific value further increases due to side reaction, in which Cox is generated, when a high-temperature reaction condition is applied to facilitate a reaction process system, decrease in the activity and performance of a catalyst is accelerated.

To address the above problems, various technologies, such as a technology of using zeolite with a porous molecular structure as a support for a catalyst or a technology of coating a surface of a catalyst with zeolite, have been reported. However, since zeolite has very fine pores, relief effect thereof on heat generation is very small. Therefore, a catalyst that may more effectively relieve heat generation due to high-temperature and high-pressure reaction conditions and side reaction urgently needs to be developed.

RELATED ART DOCUMENT

[Patent Document] (Patent Document 1) U.S. Pat. No. 5,041,401A

DISCLOSURE

Technical Problem

Therefore, the present invention has been made in view of the above problems, and it is one object of the present invention to provide a catalyst for oxidative dehydrogenation having a porous structure which may easily control heat generation due to high-temperature and high-pressure reaction conditions and side reaction due to the porous structure and thus exhibits superior product selectivity.

It is another object of the present invention to provide a method of preparing the catalyst for oxidative dehydrogenation.

The above and other objects can be accomplished by the present disclosure described below.

Technical Solution

In accordance with an aspect of the present invention, the above and other objects can be accomplished by the provision of a catalyst for oxidative dehydrogenation, including a porous aluminum silicate support and a metal oxide having a composition represented by Formula 1 below:

$$AB_2O_4 \qquad \text{[Formula 1]}$$

wherein A is one or more selected from the group consisting of divalent cation metals and B is one or more selected from the group consisting of trivalent cation metals.

In accordance with another aspect of the present invention, there is provided a method of preparing a catalyst for oxidative dehydrogenation, the method including: a step of immersing a porous rubber in aluminum silicate to be coated with the aluminum silicate; a step of firing the porous rubber coated with the aluminum silicate; a step of obtaining a porous aluminum silicate support; a step of preparing a co-precipitated slurry including a catalyst slurry, which includes a metal oxide, or a precursor of the metal oxide; a step of immersing the porous aluminum silicate support in the catalyst slurry or the co-precipitated slurry to be coated with the catalyst slurry or the co-precipitated slurry; and a step of firing the porous aluminum silicate support coated with the catalyst slurry or the co-precipitated slurry.

Advantageous Effects

As apparent from the above description, the present invention provides a catalyst for oxidative dehydrogenation having a porous structure which may easily control heat generation due to high-temperature and high-pressure reaction conditions and side reaction due to the porous structure and thus exhibits superior product selectivity, and a method of preparing the catalyst.

DESCRIPTION OF DRAWINGS

FIG. 1 illustrates actual images of a porous rubber, a porous aluminum silicate support, and a catalyst for oxidative dehydrogenation according to the preparation process of the present invention.

BEST MODE

Hereinafter, the present invention is described in detail.

The present inventors have continued research into a catalyst for oxidative dehydrogenation. As a result, the present inventors confirmed that, when a catalyst support is prepared using a porous rubber, heat generation due to high-temperature and high-pressure reaction conditions and side reaction is alleviated and thus high selectivity for a product is maintained, thereby completing the present invention.

Hereinafter, the catalyst for oxidative dehydrogenation according to the present invention is described in detail.

The catalyst for oxidative dehydrogenation includes a porous aluminum silicate support and a metal oxide having a composition represented by Formula 1 below:

$$AB_2O_4 \quad \text{[Formula 1]}$$

wherein A may be, for example, one or more selected from the group consisting of divalent cation metals, particularly one or more selected from the group consisting of Cu, Ra, Ba, Sr, Ca, Be, Zn, Mg, Mn, Co, and Fe (II), preferably one or more selected from the group consisting of Zn, Mg, Mn and Co, and B may be, for example, one or more selected from the group consisting of trivalent cation metals, particularly one or more selected from the group consisting of Al, Fe(III), Cr, Ga, In, Ti, La, and Ce, preferably one or more selected from the group consisting of Al, Fe (III) and Cr.

The metal oxide having the composition represented by Formula 1 may be, for example, a metal oxide having a spinel structure. The spinel structure may be understood as a structure wherein a unit lattice of a cubic system is composed of 8 divalent cations, 16 trivalent cations, and 32 oxygen ions, the oxygen ions mostly forming a face-centered cubic lattice and the divalent cations (A) and the trivalent cations (B) filling spaces between the oxygen ions.

The metal oxide may be included in an amount of, for example, 1 to 50% by weight, 1 to 30% by weight, 5 to 30% by weight, 2 to 15% by weight, or 5 to 15% by weight based on the catalyst for oxidative dehydrogenation. Within this range, oxidative dehydrogenation is initiated.

The porous aluminum silicate support may be, for example, a sponge-type support. In this case, heat generation due to high-temperature and high-pressure reaction conditions and side reaction may be easily controlled.

The aluminum silicate of the porous aluminum silicate support may be, for example, one or more selected from the group consisting of metal oxides, metal carbides, metal nitrides, and hydrated aluminum silicates. As another example, the aluminum silicate may be a kaolin-based mineral. Particularly, the aluminum silicate may be one or more selected from the group consisting of kaolinite, dickite, nacrite, halloysite, cordierite, diatomite, aluminum nitride (AlN), silicon nitride ($Si_3N_4$), silicon carbide (SiC), zirconium carbide (ZrC), tungsten carbide (WC), alumina ($Al_2O_3$), mullite, and zirconia ($ZrO_2$). In this case, since the aluminum silicate cannot be oxidatively dehydrogenated or has very low catalytic activity, the aluminum silicate effectively functions as a physical support that is noncompetitive with a metal oxide of a catalyst.

The porous aluminum silicate support may have, for example, a pore distribution of 1 to 500 ppi (pores per inch), 1 to 300 ppi, or 1 to 100 ppi. Within this range, high selectivity for a product during oxidative dehydrogenation may be maintained.

An average particle diameter of pores of the porous aluminum silicate support may be, for example, 0.2 to 10 mm, 0.5 to 5 mm, 1 to 5 mm, or 0.5 to 3 mm Within this range, adsorption and desorption of gaseous reactants and a product to and from a surface of a catalyst are facilitated, whereby the flow of gas is smoothed.

The porosity of the porous aluminum silicate support may be, for example, 10 to 99%, 30 to 98%, 70 to 99%, or 70 to 98% with respect to a total volume of the porous aluminum silicate support. Here, the porosity is calculated from a pore volume measured by a liquid impregnation method. Within this range, since retention of heat generated by exothermic reaction is alleviated, heat generated by the exothermic reaction may be effectively controlled, whereby high selectivity for a product is maintained.

A pore volume of the porous aluminum silicate support may be, for example, 0.1 to 120 $cm^3/g$, 0.1 to 60 $cm^3/g$, 20 to 60 $cm^3/g$, 0.1 to 45 $cm^3/g$, 5 to 45 $cm^3/g$, or 0.1 to 10 $cm^3/g$. Here, the pore volume is calculated from a pore volume measured by a liquid impregnation method.

The catalyst for oxidative dehydrogenation may be, for example, a sponge-type catalyst. In this case, heat generation due to high-temperature and high-pressure reaction conditions and side reaction may be easily controlled.

The catalyst for oxidative dehydrogenation may have, for example, a pore distribution of 1 to 500 ppi, 1 to 300 ppi, or 1 to 100 ppi. Within this range, high selectivity for a product may be maintained during oxidative dehydrogenation.

An average particle diameter of pores of the catalyst for oxidative dehydrogenation may be, for example, 1 to 10 mm, 1 to 5 mm, or 1 to 3 mm. Within this range, high selectivity adsorption and desorption of gaseous reactants and a product to and from a surface of a catalyst are facilitated, whereby the flow of gas is smoothed.

The porosity of the catalyst for oxidative dehydrogenation may be, for example, 10 to 99%, 30 to 98%, 70 to 99%, or 70 to 98% with respect to a total volume of the catalyst. Here, the porosity is calculated from a pore volume measured by a liquid impregnation method. Within this range, since retention of heat generated by exothermic reaction is alleviated, heat generated by the exothermic reaction is effectively controlled and thus high product selectivity is maintained.

A pore volume of the catalyst for oxidative dehydrogenation may be, for example, 0.1 to 120 $cm^3/g$, 0.1 to 60 $cm^3/g$, 20 to 60 $cm^3/g$, 0.1 to 45 $cm^3/g$, 5 to 45 $cm^3/g$, or 0.1 to 10 $cm^3/g$. Here, the pore volume may be calculated from a pore volume measured by a liquid impregnation method.

The oxidative dehydrogenation refers to a reaction wherein olefin is reacted with oxygen in the presence of a metal oxide to generate a conjugated diene and water. In a specific example, the oxidative dehydrogenation reaction may be a reaction wherein butene is reacted with oxygen to generate 1,3-butadiene and water.

A reactor used for the oxidative dehydrogenation is not specifically limited so long as the reactor is a reactor able to be used in oxidative hydrogenation. For example, the reactor may be a reactor wherein reaction temperature of an installed catalyst layer is constantly maintained, and oxidative dehydrogenation proceeds while reactants continuously pass through a catalyst layer. In a particular example, the reactor may be a tubular reactor, a tank reactor, a fluidized bed reactor, or a fixed bed reactor. Here, the fixed bed reactor may be, for example, a multi-tubular reactor or a plate-type reactor.

A product of the oxidative dehydrogenation may be, for example, one or more selected from the group consisting of butane, isobutane, 1-butene, trans-2-butene, and cis-2-butene and oxygen. The product may further include nitrogen and steam.

The amount of the oxygen may be, for example, 0.5 to 5 moles, 0.5 to 3 moles, or 0.6 to 1.5 moles based on 1 mole of the reactants. The amount of the nitrogen may be, for example, 0 to 30 moles, 2 to 25 moles, or 2 to 15 moles based on 1 mole of the reactants, and the amount of the steam may be, for example, 2 to 50 moles, 3 to 30 moles, or 4 to 25 moles based on 1 mole of the reactants. Within this range, superior catalytic activity is exhibited.

During the oxidative dehydrogenation, a gas hourly space velocity (GHSV) may be, for example, 200 to 30,000, 250 to 25,000, or 250 to 20,000 with respect to the reactants.

During the oxidative dehydrogenation, a reaction temperature (T) may be, for example, 300 to 500° C., 320 to 400° C., or 320 to 380° C.

During the oxidative dehydrogenation, a reaction pressure may be, for example, 0 to 10 bar, 0 to 5 bar, or 0 to 3 bar.

1,3-butadiene selectivity of the catalyst for oxidative dehydrogenation may be, for example, 80% or more, 85 to 99.9%, 85 to 93%, or 93 to 99.9%.

A method of preparing the catalyst for oxidative dehydrogenation according to the present invention includes a step of immersing a porous rubber in aluminum silicate to be coated with the aluminum silicate; a step of firing the porous rubber coated with the aluminum silicate; a step of obtaining a porous aluminum silicate support; a step of preparing a co-precipitated slurry including a catalyst slurry, which includes a metal oxide, or a precursor of the metal oxide; a step of immersing the porous aluminum silicate support in the catalyst slurry or the co-precipitated slurry to be coated with the catalyst slurry or the co-precipitated slurry; and a step of firing the porous aluminum silicate support coated with the catalyst slurry or the co-precipitated slurry.

The step of immersing the porous rubber in aluminum silicate to be coated with the aluminum silicate may include a step of preparing an aluminum silicate slurry; a step of immersing a porous rubber in the aluminum silicate slurry to be coated with the aluminum silicate slurry; and a step of aerating and drying the aluminum silicate slurry-coated porous rubber.

The aluminum silicate slurry may be prepared, for example, by diluting aluminum silicate with water.

A weight ratio of the aluminum silicate:water may be, for example, 10:1 to 1:10, 8:1 to 1:8, or 5:1 to 1:5. Within this range, the porous rubber may be entirely coated with the aluminum silicate.

The aluminum silicate slurry may include, for example, a binder for increasing viscosity in an amount of 0.01 to 10% by weight, 0.01 to 8% by weight, or 0.01 to 5% by weight. The binder may be, for example, one or more selected from the group consisting of polyvinyl alcohol, starch, carboxymethylcellulose, dextrin, wax emulsion, polyethylene glycol, lignosulfonate, methylcellulose, paraffin, and polyacrylate. In this case, adhesion of aluminum silicate to the porous rubber may be increased.

The porous rubber may be immersed, for example, during a period during which the aluminum silicate slurry contacts an entire area of the porous rubber. Here, the period may be, without being specifically limited, 0.1 to 30 min, 0.1 to 10 min, or 0.1 to 1 min.

The aerating refers to blowing a gas into the porous rubber coated with the aluminum silicate slurry such that the aluminum silicate slurry does not block pores of the porous rubber. Here, the gas may be, for example, air, nitrogen, helium, or argon. The pressure and temperature of the gas are not specifically limited so long as the coating effect is maintained.

The porous rubber coated with the aluminum silicate slurry may be dried, for example, at 80 to 160° C., 90 to 150° C., or 100 to 140° C. and for 0.5 to 24 hours, 0.5 to 16 hours, or 0.5 to 3 hours. Within this range, moisture is completely removed.

Each of the step of immersing the porous rubber in the aluminum silicate slurry to be coated with the aluminum silicate slurry and the step of aerating and drying the aluminum silicate slurry-coated porous rubber may be repeated 1 to 10 times, or 1 to 5 times.

The porous rubber coated with the aluminum silicate may be fired, for example, at 1,000 to 2,000° C., 1,200 to 1,800° C., or 1,400 to 1,800° C. for 1 to 10 hours, or 1 to 5 hours. Within this range, alpha alumina is formed inside the porous aluminum silicate support, whereby strength and durability increase.

The porous rubber may be combusted, for example, at 300 to 800° C., 350 to 700° C., or 400 to 660° C. during firing. In this case, the porous rubber does not remain in the porous aluminum silicate support.

The porous rubber is not specifically limited so long as it may be used as a foam. For example, the porous rubber may be polyurethane. In this case, large pores are easily formed.

The catalyst slurry may be prepared by, for example, by diluting a metal oxide having a composition represented by Formula 1 below with water:

   [Formula 1]

wherein A may be, for example, one or more selected from the group consisting of divalent cation metals, particularly one or more selected from the group consisting of Cu, Ra, Ba, Sr, Ca, Be, Zn, Mg, Mn, Co, and Fe (II), preferably one or more selected from the group consisting of Zn, Mg, Mn and Co, and B may be, for example, one or more selected from the group consisting of trivalent cation metals, particularly one or more selected from the group consisting of Al, Fe(III), Cr, Ga, In, Ti, La, and Ce, preferably one or more selected from the group consisting of Al, Fe (III) and Cr.

A weight ratio of the metal oxide:water may be, for example, 10:1 to 1:10, 8:1 to 1:8, or 5:1 to 1:5. Within this range, the porous aluminum silicate support may be entirely coated with the metal oxide.

The metal oxide, for example, may have a powder form and may be prepared through a coprecipitation step, a filtration step, a drying step, and a firing step. In a particular example, the metal oxide may be prepared through (1) a step of preparing a catalyst precursor solution including divalent and trivalent cation metal precursors; (2) a step of adding the catalyst precursor solution dropwise to an aqueous ammonia solution at 10 to 50° C. (pH 7 to 10); (3) a step of stirring the aqueous ammonia solution, to which the catalyst precursor solution has been added, while maintaining pH of the aqueous ammonia solution such that coprecipitation occurs; (4) a step of vacuum filtering a co-precipitated solution to obtain a co-precipitate; (5) a step of drying the obtained co-precipitate at 60 to 150° C. for 6 to 30 hours; and (6) a step of elevating temperature to 400 to 800° C. at a heating rate of 0.5 to 10° C./min and then maintaining the elevated temperature for 2 to 16 hours such that firing is performed.

The metal precursors of the step (1) are not specifically limited so long as they are generally used. For example, the metal precursors may be metal salts including divalent or trivalent cation metal ingredients. In a particular example, the metal precursors may be nitrates, ammonium salts, sulfates, or chlorides of the divalent or trivalent cation metal ingredients. In the step (3), pH may be maintained, for example, by simultaneously adding an additional aqueous ammonia solution dropwise when the aqueous catalyst precursor solution is added dropwise.

The co-precipitated slurry including the metal oxide precursor may be prepared, for example, by co-precipitating the metal oxide having the composition represented by Formula 1 with a catalyst precursor in the same stoichiometric ratio.

The co-precipitated slurry may be prepared, for example, through (1') a step of preparing a catalyst precursor solution including divalent and trivalent cation metal precursors; (2') a step of adding the catalyst precursor solution dropwise to an aqueous ammonia solution at 10 to 50° C. (pH 7 to 10); (3') a step of stirring the aqueous ammonia solution, to which the catalyst precursor solution has been added dropwise, for 30 minutes to 24 hours while maintaining pH of the aqueous ammonia solution such that coprecipitation occurs; and (4') a step of vacuum filtering a resultant co-precipitated solution to adjust the concentration of a co-precipitated slurry.

The metal precursors of the step (1') are not specifically limited so long as they are generally used. For example, the metal precursors may be metal salts including a divalent or trivalent cation metal ingredient. In a particular example, the metal precursors may be nitrates, ammonium salts, sulfates, or chlorides of the metal ingredient. The concentration of the catalyst precursor solution may be, for example, 1 to 70% by weight, 2 to 50% by weight, or 3 to 30% by weight. When a co-precipitate is fired within this range, the composition represented by Formula 1 is provided. In the step (3'), pH may be maintained, for example, by simultaneously adding an additional aqueous ammonia solution dropwise when the aqueous catalyst precursor solution is added dropwise. In the step (4'), a concentration ratio by weight of the co-precipitated slurry:the sum of the co-precipitate and water may be, for example, 10:1 to 1:10, 8:1 to 1:8, or 5:1 to 1:5. Within this range, the porous aluminum silicate support is entirely coated with the co-precipitate.

The co-precipitated slurry may include, for example, a binder for increasing viscosity (binder) in an amount of 0.01 to 10% by weight, 0.01 to 8% by weight, or 0.01 to 5% by weight. The binder may be, for example, one or more selected from the group consisting of polyvinyl alcohol, starch, carboxymethylcellulose, dextrin, wax emulsion, polyethylene glycol, lignosulfonate, methylcellulose, paraffin, and polyacrylate. In this case, adhesion of the co-precipitate to the porous aluminum silicate support may be increased.

The step of immersing the porous aluminum silicate support in the catalyst slurry or the co-precipitated slurry to be coated with the catalyst slurry or the co-precipitated slurry may include a step of immersing the porous aluminum silicate support in the catalyst slurry or the co-precipitated slurry; and a step of aerating and drying the porous aluminum silicate support coated with the catalyst slurry or the co-precipitated slurry.

The porous aluminum silicate support may be immersed, for example, during a period during which the catalyst slurry or the co-precipitated slurry contacts an entire area of the porous aluminum silicate support. Here, the period may be, without being specifically limited, 0.1 to 30 min, 0.1 to 10 min, or 0.1 to 1 min.

The aerating refers to blowing a gas into the porous aluminum silicate support coated with the catalyst slurry or the co-precipitated slurry such that the catalyst slurry or the co-precipitated slurry does not block pores of the porous rubber. Here, the gas may be, for example, air, nitrogen, helium, or argon. The pressure and temperature of the gas are not specifically limited so long as the coating effect is maintained.

The porous aluminum silicate support coated with the catalyst slurry or the co-precipitated slurry may be dried, for example, at 80 to 160° C., 90 to 150° C., or 100 to 140° C. and for 0.5 to 24 hours, 0.5 to 16 hours, or 0.5 to 3 hours. Within this range, moisture is completely removed.

Each of the step of immersing the porous aluminum silicate support in the catalyst slurry or the co-precipitated slurry; and the step of aerating and drying the porous aluminum silicate support coated with the catalyst slurry or the co-precipitated slurry ⇌ aerate and drying may be repeatedly performed 1 to 10 times or 1 to 5 times.

The porous aluminum silicate support coated with the catalyst slurry or the co-precipitated slurry may by fired by any method used to prepare a catalyst for oxidative dehydrogenation without specific limitation. For example, the firing may be performed by elevating temperature up to 400 to 800° C., or 450 to 750° C. at a heating rate of 0.5 to 10° C./min, 0.5 to 5° C./min, or 0.5 to 3° C./min and then maintaining the elevated temperature for 2 to 16 hours, or 3 to 9 hours.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

Example

Example 1

<Preparation of Porous Aluminum Silicate Support>

Kaolinite ($Al_2Si_2O_5(OH)_4$) and maltodextrin were mixed in a weight ratio of 1:1, thereby preparing a slurry. A polyurethane foam, as a porous rubber having a pore distribution of 15 ppi (pores per inch), was immersed in the slurry to coat the polyurethane foam. Here, aeration was performed such that the pores were not blocked, and then drying was performed at 120° C. for 1 hour or more. The dried polyurethane foam was immersed in the slurry again, and aeration and drying were repeated four times. Subsequently, firing was performed at 1,600° C. for two hours, thereby preparing a porous aluminum silicate support.

<Preparation of Metal Oxide and Catalyst Slurry>

12 g of zinc chloride ($ZnCl_2$) and 48 g of ferric chloride ($FeCl_3$) were dissolved in distilled water, thereby preparing a metal precursor solution. Here, a mole ratio of metal ingredients included in the metal precursor solution was as follows: Zn:Fe=1:2. The prepared metal precursor solution and an aqueous ammonia solution, which was used to maintain pH 9, were simultaneously added to an aqueous ammonia solution at pH 9 and room temperature dropwise, followed by stirring for 1 hour to be co-precipitated. Subsequently, the co-precipitated solution was vacuum filtered to obtain a co-precipitate. The obtained co-precipitate was dried at 90° C. for 16 hours and then temperature was elevated from 80° C. up to 650° C. at a heating rate of 1° C./min under an air atmosphere. The elevated temperature was maintained for six hours, thereby preparing a zinc-iron oxide ($ZnFe_2O_4$) powder having a spinel structure. The prepared metal oxide powder was pulverized to a size of 250 μm or less. The pulverized metal oxide powder was diluted with water in a weight ratio of 1:1, thereby preparing a catalyst slurry.

<Preparation of Catalyst for Oxidative Dehydrogenation>

The prepared porous aluminum silicate support was immersed in the prepared catalyst slurry and then aeration was performed. Subsequently, drying was performed at 120° C. for one hour. Subsequently, the dried porous aluminum silicate support was immersed in a catalyst slurry again, and then aeration and drying were repeated three times. An obtained catalyst was dried at 120° C. for 16 hours, and temperature was elevated from 80° C. up to 650° C. at a heating rate of 1° C./min under an air atmosphere. The elevated temperature was maintained for four hours, thereby preparing a catalyst for oxidative dehydrogenation having a porous structure.

Example 2

An experiment was carried out in the same manner as in Example 1, except that, when a porous aluminum silicate support was prepared, a polyurethane foam, as a porous rubber having a pore distribution of 10 ppi (pores per inch), was used instead of the polyurethane foam as a porous rubber having a pore distribution of 15 ppi.

Example 3

An experiment was carried out in the same manner as in Example 1, except that, when a porous aluminum silicate support was prepared, a polyurethane foam, as a porous rubber having a pore distribution of 45 ppi (pores per inch) was used instead of the polyurethane foam as a porous rubber having a pore distribution of 15 ppi.

Example 4

An experiment was carried out in the same manner as in Example 1, except that, when a metal oxide was prepared, a metal precursor solution was prepared by dissolving 12 g of zinc chloride ($ZnCl_2$), 42 g of iron nitrate ($FeNO_3$), and 6 g of aluminum chloride ($AlCl_3$), instead of 12 g of zinc chloride ($ZnCl_2$) and 48 g of ferric chloride ($FeCl_3$), in distilled water. Here, a mole ratio of metal ingredients included in the metal precursor solution was as follows: Zn:Fe:Al=1:1.75:0.25.

Example 5

An experiment was carried out in the same manner as in Example 1, except that, when a metal oxide was prepared, a metal precursor solution was prepared by dissolving 18 g of magnesium nitrate ($MgNO_3$) and 48 g of ferric chloride ($FeCl_3$), instead of 12 g of zinc chloride ($ZnCl_2$) and 48 g of ferric chloride ($FeCl_3$), in distilled water. Here, a mole ratio of metal ingredients included in the metal precursor solution was as follows: Mg:Fe=1:2.

Example 6

An experiment was carried out in the same manner as in Example 1, except that, when a metal oxide was prepared, a metal precursor solution was prepared by dissolving 18 g of manganese nitrate ($MnNO_3$) and 48 g of ferric chloride ($FeCl_3$), instead of 12 g of zinc chloride ($ZnCl_2$) and 48 g of ferric chloride ($FeCl_3$), in distilled water. Here, a mole ratio of metal ingredients included in the metal precursor solution was as follows: Mn:Fe=1:2.

Example 7

An experiment was carried out in the same manner as in Example 1, except that a co-precipitated slurry was obtained by vacuum filtering a co-precipitated solution when a metal oxide and a catalyst slurry were prepared, and the prepared porous aluminum silicate support was immersed in the prepared co-precipitated slurry when a catalyst for oxidative dehydrogenation was prepared.

Comparative Example 1

A metal oxide was prepared in the same manner as in Example 1. That is, a co-precipitate was obtained by vacuum filtering a co-precipitated solution, and the obtained co-precipitate was dried at 90° C. for 16 hours, followed by pulverizing the dried co-precipitate into a powder. This powder was mixed and kneaded with water and maltodextrin, followed by extruding by means of a screw-type rotor. The extruded product was cut to a size of 5 mm and then dried, thereby preparing a catalyst having a cylindrical pellet shape. Temperature was elevated from 80° C. to 650° C. at a heating rate of 1° C./min under an air atmosphere. The elevated temperature was maintained for six hours to fire the catalyst. As a result, a pellet-shaped catalyst was prepared.

Test Example

Butadiene was prepared using the catalyst for oxidative dehydrogenation prepared according to each of Examples 1 to 7 and Comparative Example 1. Results are summarized in Table 1 below.

Butadiene Preparation

A mixture of 1-butene, trans-2-butene, and cis-2-butene and oxygen were used as reactants, and nitrogen and steam were additionally introduced along with the reactants. Here, a metallic tubular fixed-bed reactor was used. A reactant ratio and a gas hourly space velocity (GHSV) were determined based on a butene mixture as summarized in Table 1 below. The metallic tubular fixed-bed reactor was filled with 10 cc of each of the catalysts of the examples and the comparative example, and steam was introduced in a water form thereinto. Here, the steam was vaporized at 150° C. by means of a vaporizer and mixed with the reactants, i.e., the butene mixture and the oxygen, such that the steam was flowed along with the reactants into the reactor. After reaction, a product was analyzed using gas chromatography (GC). The conversion rate (X_butene), selectivity (S_1,3-butadiene, S_$CO_x$), and yield of a butene mixture were calculated according to Mathematical Equations 1 to 3 below using results measured by gas chromatography:

Conversion rate (%)=(moles of reacted butene/moles of supplied butene)×100 [Mathematical Equation 1]

Selectivity (%)=(moles of generated 1,3 butadiene or CO$_x$/moles of reacted butene)×100 [Mathematical Equation 2]

Yield (%)=(moles of generated 1,3 butadiene/moles of supplied butene)×100 [Mathematical Equation 3]

TABLE 1

| Classification | | Examples | | | | | | | Comparative example |
|---|---|---|---|---|---|---|---|---|---|
| | | 1 | 2 | 3 | 4 | 5 | 6 | 7 | 1 |
| Reaction conditions | Car (ppi) | 15 | 10 | 45 | 15 | 15 | 15 | 15 | — |
| | GHSV (hr$^{-1}$$_{butene}$) | 250 | 250 | 250 | 250 | 250 | 250 | 250 | 250 |
| | T (° C.) | 340 | 360 | 340 | 340 | 340 | 340 | 340 | 340 |
| | O$_2$/butene | 0.75 | 0.75 | 0.75 | 0.75 | 0.75 | 0.75 | 0.75 | 0.75 |
| | Steam/butene | 15 | 15 | 15 | 15 | 15 | 15 | 15 | 15 |
| | N$_2$/butene | 3 | 3 | 3 | 3 | 3 | 3 | 3 | 3 |
| Reaction results | X_butene | 32.3 | 49.0 | 39.9 | 56.6 | 34.6 | 40.0 | 24.4 | 49.8 | 46.11 |
| | S_1,3-butadiene | 96.3 | 94.9 | 92.8 | 90.6 | 89.8 | 84.8 | 88.4 | 95.6 | 92.24 |
| | Yield | 31.1 | 46.5 | 37.0 | 51.2 | 31.1 | 33.9 | 21.6 | 47.6 | 42.53 |
| | S_CO$_2$ | 2.2 | 4.1 | 6.1 | 7.5 | 8.4 | 11.9 | 10.1 | 3.1 | 6.33 |

As shown in Table 1, it can be confirmed that, in the cases of Example 1 to 7 in which the catalyst having a porous structure prepared according to the present invention was used, butene conversion rate, butadiene selectivity, and yield are all superior.

On the other hand, it can be confirmed that, in the case of Comparative Example 1 in which a pellet-shaped catalyst was used using a metal oxide having the same composition as that of Example 1, butene conversion rate, butadiene selectivity, and yield are all poor, compared to the case of the Example 1.

Reference Example

Butadiene of a test example was prepared as follows. The catalyst for oxidative dehydrogenation prepared according to Example 1 was used, and 02, steam, and N$_2$ were injected in a mole ratio of 1:4:12 with respect to 1 mol of butene at a reaction temperature (T) of 360° C. such that reaction occurred. As result, X_butene was 56.56, S_1,3-butadiene was 90.55, a yield was 51.22, and S_CO$_x$ was 7.46. From these results, it can be confirmed that catalytic activity improves as the ratio of steam to the butene mixture increases.

From these results, the present inventors confirmed that, when a porous catalyst was prepared using a porous rubber, heat generation due to high-temperature and high-pressure reaction conditions and side reaction is alleviated, whereby high selectivity for a product may be maintained.

The invention claimed is:

1. A method of preparing a catalyst for oxidative dehydrogenation, the method comprising:
   a step of immersing a porous rubber in aluminum silicate to be coated with the aluminum silicate;
   a step of firing the porous rubber coated with the aluminum silicate to obtain a porous aluminum silicate support, wherein a temperature of firing the porous rubber coated with aluminum silicate is 1,400 to 1,8000C;
   a step of preparing a catalyst slurry comprising a metal oxide, or preparing a co-precipitated slurry comprising a precursor of the metal oxide;
   a step of immersing the porous aluminum silicate support in the catalyst slurry or the co-precipitated slurry to be coated with the catalyst slurry or the co-precipitated slurry; and
   a step of firing the porous aluminum silicate support coated with the catalyst slurry or the co-precipitated slurry,
   wherein the metal oxide is represented by Formula 1:

AB$_2$O$_4$      [Formula 1]

wherein A is Zn and B is Fe (III), and
   wherein the porous aluminum silicate support has a pore distribution of 10 ppi to 45 ppi (pores per inch).

2. The method according to claim 1, wherein the step of immersing the porous rubber in aluminum silicate to be coated with the aluminum silicate comprises: a step of preparing an aluminum silicate slurry; a step of immersing the porous rubber in the aluminum silicate slurry to be coated with the aluminum silicate slurry; and a step of aerating and drying the aluminum silicate slurry-coated porous rubber.

3. The method according to claim 1, wherein the porous rubber is combusted at 300 to 800° C. during firing.

4. The method according to claim 1, wherein the porous rubber is polyurethane.

5. The method according to claim 1, wherein the catalyst slurry is prepared by diluting the metal oxide of Formula 1 with water.

6. The method according to claim 5, wherein a weight ratio of the metal oxide:the water is 10:1 to 1:10.

7. The method according to claim 1, wherein the step of immersing the porous aluminum silicate support in the catalyst slurry or the co-precipitated slurry to be coated with the catalyst slurry or the co-precipitated slurry comprises: a step of immersing the porous aluminum silicate support in the catalyst slurry or the co-precipitated slurry; and a step of aerating and drying the porous aluminum silicate support coated with the catalyst slurry or the co-precipitated slurry.

8. The method according to claim 7, wherein the porous aluminum silicate support coated with the catalyst slurry or the co-precipitated slurry is dried at 80 to 160° C. for 0.5 to 24 hours.

9. The method according to claim 1, wherein, to fire the porous aluminum silicate support coated with the catalyst slurry or the co-precipitated slurry, a temperature is elevated up to an elevated temperature of 400° C. to 800° C. at a heating rate of 0.5° C./min to 10° C./min and then the elevated temperature is maintained for 2 to 16 hours.

10. The method according to claim 1, wherein an average particle diameter of pores of the porous aluminum silicate support is 1 mm to 5 mm.

\* \* \* \* \*